United States Patent [19]
Dickinson et al.

[11] Patent Number: 6,050,958
[45] Date of Patent: *Apr. 18, 2000

[54] GUIDE WIRE FOR A CATHETER WITH POSITION INDICATING MEANS

[75] Inventors: Robert Julian Dickinson; Martin Terry Rothman, both of London, United Kingdom

[73] Assignee: Intravascular Research Limited, Isleworth, United Kingdom

[*] Notice: This patent is subject to a terminal disclaimer.

[21] Appl. No.: 08/936,469

[22] Filed: Sep. 22, 1997

Related U.S. Application Data

[62] Division of application No. 08/659,091, Jun. 4, 1996, Pat. No. 5,669,878, which is a continuation of application No. 08/256,980, Jul. 29, 1994.

[30] Foreign Application Priority Data

Jan. 30, 1992 [GB] United Kingdom .................. 9202031
Jan. 28, 1993 [WO] WIPO ..................... PCT/GB93/00189

[51] Int. Cl.[7] ........................................................ A61B 5/00
[52] U.S. Cl. .......................... 600/585; 604/164; 604/528; 604/529
[58] Field of Search .............................. 604/95, 164, 170, 604/264, 93, 523, 528, 529; 600/434, 435, 585

[56] References Cited

U.S. PATENT DOCUMENTS

| | | |
|---|---|---|
| 4,327,722 | 5/1982 | Groshong et al. . |
| 4,419,095 | 12/1983 | Nebergall et al. . |
| 4,554,929 | 11/1985 | Samson et al. . |
| 4,671,291 | 6/1987 | Wilson . |
| 4,766,905 | 8/1988 | Namekawa . |
| 4,838,879 | 6/1989 | Tanabe et al. . |
| 4,867,173 | 9/1989 | Leoni . |
| 4,899,757 | 2/1990 | Pope, Jr. et al. . |
| 4,917,094 | 4/1990 | Lynch et al. . |
| 4,922,924 | 5/1990 | Gambale et al. . |
| 4,951,686 | 8/1990 | Herlitze . |
| 4,991,588 | 2/1991 | Pflueger et al. . |
| 4,991,602 | 2/1991 | Amplatz et al. ........................ 604/164 |
| 5,034,005 | 7/1991 | Appling . |
| 5,081,993 | 1/1992 | Kitney et al. . |
| 5,084,022 | 1/1992 | Claude . |
| 5,174,302 | 12/1992 | Palmer . |
| 5,253,653 | 10/1993 | Daigle et al. ........................... 604/164 |
| 5,257,629 | 11/1993 | Kitney et al. . |
| 5,669,878 | 9/1997 | Dickenson et al. ....................... 604/95 |

FOREIGN PATENT DOCUMENTS

| | | |
|---|---|---|
| 0050606 | 4/1982 | European Pat. Off. . |
| 0145489 | 6/1985 | European Pat. Off. . |
| 0063859 | 11/1985 | European Pat. Off. . |
| 0227906 | 7/1987 | European Pat. Off. . |
| 1511269 | 5/1978 | United Kingdom . |
| 1555799 | 11/1979 | United Kingdom . |
| 2028136 | 3/1980 | United Kingdom . |
| 2048678 | 12/1980 | United Kingdom . |
| 2083182 | 3/1982 | United Kingdom . |
| WO81/00676 | 3/1981 | WIPO . |
| WO89/04142 | 5/1989 | WIPO . |
| WO91/17710 | 11/1991 | WIPO . |
| WO93/15498 | 8/1993 | WIPO . |

OTHER PUBLICATIONS

H.B. Meire et al, "Ultrasonic recording of fetal breathing", British Journal of Radiology, vol. 48, pp. 477–480, 1975.

K. Lindstrom et al, "Device for measurement of fetal breathing movements–I" Ultrasound Med. Biol., vol. 3, pp. 143–151, 1977.

K. Marshal et al, "Device for measurement of fetal breathing movements–II", Ultrasound Med. Biol., vol. 4, pp. 13–26, 1978.

K. Lindstrom et al, "Interface for analysis of fetal breathing movements by ultrasonic real–time scanner", Ultrasonic in Medicine, vol. 3B, pp. 699–707, ISBN' D–306–34203–0, Plenum Press, New York, 1977.

K. Marshal et al, "New Ultrasonic device for monitoring fetal breathing movements", Biomedical Engineering, pp. 47–52, Feb., 1976.

*Primary Examiner*—Ronald Stright
*Assistant Examiner*—Jeremy Thissell
*Attorney, Agent, or Firm*—Richard M. Goldberg

[57] ABSTRACT

A catheter is provided either with an x-ray-opaque marker or with a device for generating a vibratory signal for transmission along a guide wire within the catheter in order to indicate the position of the catheter.

4 Claims, 1 Drawing Sheet

GUIDE WIRE FOR A CATHETER WITH POSITION INDICATING MEANS

This application is a, division, of application Ser. No. 08/659,091 filed Jun. 4, 1996, which issued into U.S. Pat. No. 5,669,878 on Sep. 23, 1997, and which is a continuation of abandoned application Ser. No. 08/256,980, filed on Jul. 29, 1994.

The present invention relates to catheters and more particularly to means for enabling the position of the tip of a catheter to be identified when it is inside a patient's body.

BACKGROUND TO THE INVENTION

There are numerous different types of catheter which are used for a multitude of medical purposes many of which involve the insertion of the catheter into a patient's body via, for example, an artery of the patient.

An example of such use is disclosed in our earlier U.S. Pat. Nos. 5,081,993 and 5,257,629. In those earlier U.S. Patents there is disclosed a catheter which has at its distal tip (distal with respect to the operating surgeon) an ultra-sonic transducer array adapted to emit ultrasonic signals and to receive their echoes in order to provide an image of the interior of the human organ in question, e.g an artery which could be inside the patient's heart.

Apart from the system disclosed in these two earlier patent specifications and the associated catheters for use in those systems, there is also the well-known balloon type catheter which is used to carry out a so-called angioplasty. This operation involves the insertion of the balloon catheter into a patient's artery, typically through the patient's thigh, and then feeding the distal end of the catheter into the damaged artery which could be within the patient's heart. Typically the damage can consist of so-called plaque or a loose part of the inside wall of the artery, as it were, hanging down into the artery thus impeding blood flow.

In carrying out an angioplasty operation the surgeon will need to accurately locate the balloon distal tip of the catheter in exactly the right position within the artery in relation to the plaque or damaged wall. Furthermore, it may be necessary for the surgeon to withdraw the tip at least to some extent and then to reposition it in the affected area.

Considerable skill, and therefore room for error, is involved in this accurate positioning of the distal end of the catheter.

The present invention is concerned with providing means whereby the surgeon can more easily locate the distal tip of the catheter in the required position within the patient or reposition that tip in the required position.

It is normal, to provide the proximal end of the catheter (proximal with respect to the surgeon) with some kind of "handle" by which the surgeon can grip the catheter in order to push it into the patient's artery and to feed it so that the distal end arrives at the desired position. It is also known to provide a catheter with some mechanical means for indicating to the surgeon the distance that the catheter has been inserted into the patient. More specifically, it is known to employ a motorised drive to pull back the catheter by a prescribed amount.

The present invention is concerned with providing improved means for indicating to the surgeon the position of the catheter within the patient and in particular the position of the distal end of the cather which distal end carries some operative device, such as a balloon, whereby the surgeon is able to effect the required treatment or operation. The distal end of the catheter could be provided with other devices/arrangements than a balloon, these device/arrangements being of many known kinds.

There is disclosed in U.S. Pat. No. 4,867,173 a catheter having a central guide wire the tip of which can be made of a radio opaque material to facilitate location of the distal end of the guide wire.

There is disclosed in European Patent Application 0050606 a dispensing container for venous catheters which container is provided with an indicator by which as the catheter is inserted into a patient the length that has been inserted can be read off.

SUMMARY OF THE INVENTION

According to the present invention, a catheter provided with a guide wire over which the catheter can be slid is characterised in that the guide wire is provided with a plurality of opaque markers set at regular intervals along the length of the wire.

According to the present invention, a catheter having a guide wire over which the catheter can be slid is characterized by the guide wire being provided with means for generating a vibratory signal for transmission along the wire whereby the distance that the catheter has been inserted into a patient can be indicated.

BRIEF DESCRIPTION OF DRAWINGS

How the invention may be carried out will now be described, by way of example only, and with reference to the accompanying drawings in which:

FIG. 1

Figure 1:
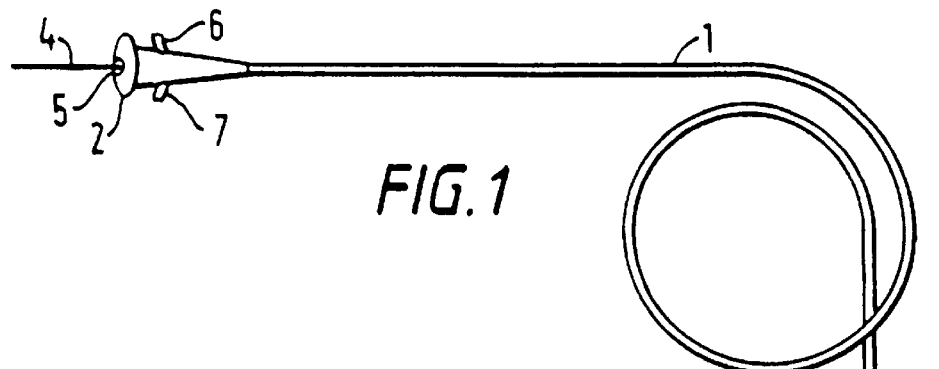
FIG. 1 shows a known type of catheter to which the present invention can be applied.
Figure 2:
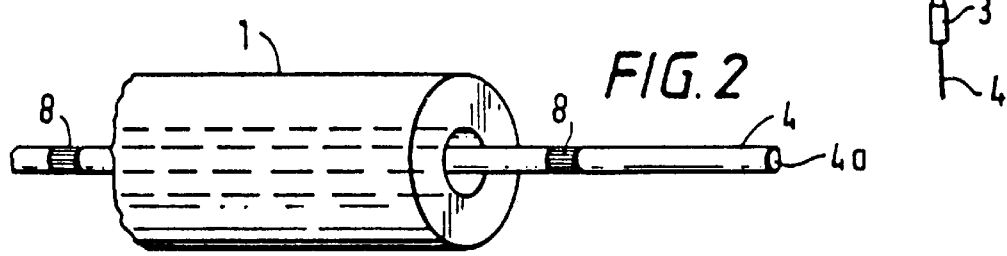
FIG. 2 is an enlarged fragmentary view of part of the catheter shown in FIG. 1 incorporating a first embodiment of the invention.

This illustrates a typical known type of catheter which consists of a plastic tube 1 which has a handle 2 at one end and a tip member 3 at the other. A guide wire 4 can be passed through the tube 1. The handle 2 is provided with an axially located aperture 5 through which the guide wire 4 can pass. The handle 2 is also provided with further radially located apertures 6 and 7 through which various treatment devices can be inserted into the catheter tube 1.

FIG. 2

In this first embodiment of the present invention parts corresponding to the parts in the known catheter of FIG. 1 have the same reference numerals.

The guide wire 4 is provided with one or more x-ray-(radio)-opaque markers 8. In a preferred arrangement the markers would be placed 1cm apart along the length of the guide wire 4 with heavier or duplicate markings at 5 cm intervals.

In use the guide wire 4 would be used to position the catheter accurately within the relevant vessel (artery) of the patient using the known x-ray equipment. By providing the markers 8 it is possible to accurately position and reposition the marker wire compared with the prior art catheter without the markers 8.

Another practical difficulty with the prior art is that it is often difficult to estimate the size of the relevant vessel (artery) due to uncertainties concerning the magnification of the visualising system and also pin cushion deformation. By providing markers of known dimensions it is easier for the surgeon to make the aforementioned size estimates.

FIG. 3

Again, in this embodiment the same elements as those in the prior art device of FIG. 1 are indicated by the same reference numerals.

In this embodiment the distal end of the catheter 1 is provided with an ultrasonic piezoelectric transducer array 9 of the kind disclosed in our U.S. patent application Ser. No. GB88/00971 (Publication No WO89/04142).

A further ultrasonic piezoelectric transducer 10 is carried by the inside of the catheter tube 1 at its distal end. The radially inner surface of the transducer 10 is in sliding contact with the outside surface of the guide wire 4.

With this kind of catheter arrangement, the central guide wire 4 is first inserted into position within the patient's vessel/artery and then the tubular catheter 1 is slid along the guidewire to bring the transducer 9 into the desired position (s) for producing a visual representation of the interior of the vessel/artery by means of the ultrasonic signals emitted from and the echoes received by the transducer array 9 in the manner described in our above-mentioned U.S. Pat. No. 5,081,993.

There are situations in which the surgeon needs to know where the distal end of the catheter is in relation to the end of the guide wire 4.

In the prior art it is known to determine the position of the distal end of the catheter in relation to the distal end of the guide wire by making some kind of measurement at the proximal end of the catheter and guide wire, i.e at the entry point. However, one of the problems with this prior art approach is that the position of the catheter in relation to the guide wire at the proximal end may not be a true measure of the position of the probe, i.e the transducer 9, in relation to the distal end 4 of the guide wire because of stretching of the plastic material from which the catheter tube is made.

In this embodiment an ultrasonic piezoelectric transducer 10 is provided mounted on the inside surface of the distal end of the catheter tube 1, the radially inner surface of transducer 10 being in slidable contact with the external surface of the metal guide wire 4. The transducer 10 is energisable through appropriate electrical leads which are not shown.

Electrical energisation of the transducer 10 will cause vibrations to be imparted to the guide wire 4, i.e, an ultrasound wave is launched into the guide wire 4. This ultrasound wave travels down the wire, in both directions, and is reflected from the distal end 4a of the glide wire. The reflected echo is then detected by the same transducer 10 which acts as a receiver.

Figure 3:
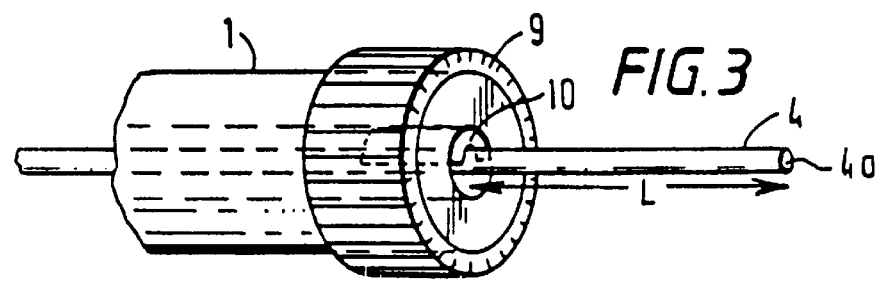
FIG. 3 is a view similar to FIG. 2 showing a second embodiment of the invention.
Figure 4:
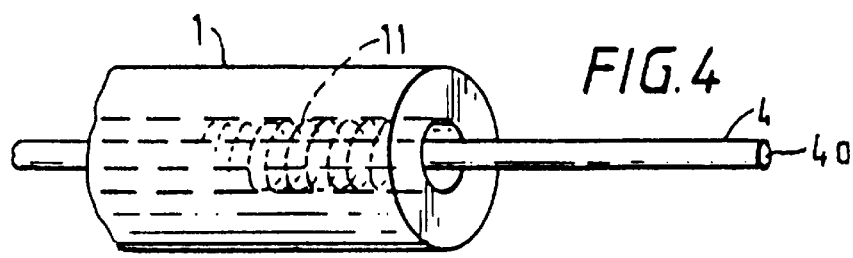
FIG. 4 is a view similar to FIG. 2 showing a third embodiment of the invention.

The time taken for the launched ultrasound wave leaving the transducer 10 to return in the form of an echo reflected from the distal end 4a of the guide wire 4 will depend upon the distance L shown in FIG. 3.

It is thus possible to obtain from the ultrasonic signal and its echoes an accurate indication of the position of the distal end 1a of the catheter in relation to the position of the distal end of the guide wire 4.

The distance L is given by the formula:

$$L = \frac{C \cdot T}{2}$$

Where C is the speed of sound in the material and T is the elapsed time between the emission of the signal and receipt of its echo.

Figure 5:
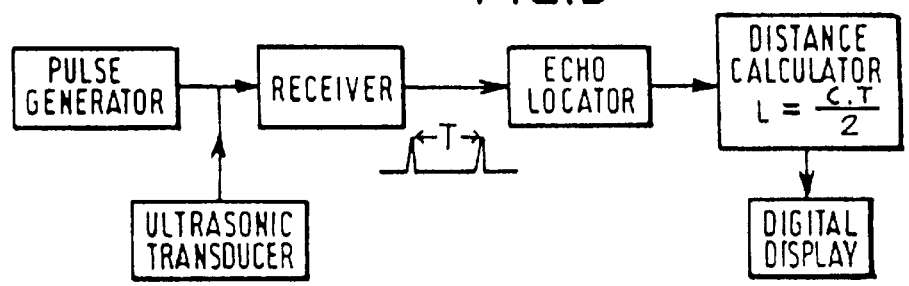
FIG. 5 is a block diagram of the arrangement for determining the distance L shown in FIG. 3.

The information which gives the distance L will be read out by an appropriate read-out means accessible to the surgeon which is shown diagrammatically in FIG. 5.

FIG. 4

This embodiment which works on a similar principle to that of FIG. 3 but instead of the ultrasonic piezoelectric transducer 10 the vibration wave is created in the guide wire 4 by means of a solenoid 11 which is mounted within the wall of the catheter tube 1 so that when energised, through appropriate lead wires (not shown), will cause a magneto-restrictive effect to generate an acoustic wave in the guide wire 4. This wave will, as in the embodiment of FIG. 3, travel to the distal end 4A of the guide wire 4, be reflected by that end and then received by the same arrangement in order to enable the distance L to be deduced and in turn presented on an appropriate visual display accessible to the surgeon.

What is claimed is:

1. A guide wire for use with and slidable within a catheter, said guide wire consisting essentially of:

a) a single uncoiled wire which is exposed in use; and b) a plurality of X-ray opaque markers set at regular intervals along said single uncoiled wire, c) each of the markers being spaced from adjacent markers by a fixed center to center distance along the length of the single wire, and d) every nth marker having a visual characteristic different from remaining ones of said markers, where n is an integer greater than one.

2. A guide wire according to claim 1, wherein said center to center distance is 1 cm and a center to center distance between every nth marker is 5 cm.

3. A guide wire according to claim 1, wherein said visual characteristic is formed by a heavier marking for every nth marker.

4. A guide wire according to claim 1, wherein said visual characteristic is formed by a duplicate marking for every nth marker.

* * * * *